United States Patent [19]
Beverley et al.

[11] Patent Number: 5,955,333
[45] Date of Patent: Sep. 21, 1999

[54] DOUBLE TARGETED GENE REPLACEMENT IN UNICELLULAR DIPLOID ORGANISMS

[75] Inventors: Stephen M. Beverley, Boston, Mass.; Angela K. Cruz, Ribeirao Preto, Brazil

[73] Assignee: President & Fellows of Harvard College, Cambridge, Mass.

[21] Appl. No.: 08/762,529

[22] Filed: Dec. 9, 1996

Related U.S. Application Data

[63] Continuation of application No. 08/489,701, Jun. 13, 1995, abandoned, which is a continuation of application No. 08/066,718, May 24, 1993, abandoned, which is a continuation-in-part of application No. 07/744,313, Aug. 13, 1991, abandoned.

[51] Int. Cl.$^6$ .............................. C12N 15/63; C12N 1/10; C12N 1/14
[52] U.S. Cl. ................................. 435/172.3; 435/254.11; 435/258.3
[58] Field of Search ........................... 435/172.3, 254.11, 435/258.3

[56] References Cited

U.S. PATENT DOCUMENTS 4,735,901  4/1988  Kurtz et al. ........................... 435/172.3
4,764,370  8/1988  Fields et al. ........................... 424/93 P

OTHER PUBLICATIONS

Norton Microbiology 2nd Ed. pp. 677–687 Addison–Wesley Publishing Co, 1986.
Kurtz et al. (1989), Mol. Gen. Genet. 217:47–52.
Hoiseth et al. (1981), Nature 291: 238–239.
Laban et al. (1990), Nature 343: 572–574.
Gritz et al. (1983), Gene 25: 179–188.
Beverley et al. (1986), Proc. Natl. Acad. Sci USA 83: 2584–2588.
Kapler, G.M. et al., "Stable Transfection of the Human Parasite *Leishmania major* Delineates a 30–Kilobase Region Sufficient for Extrachromosomal Replication and Expression", (Mar. 1990), *Molecular and Cell Biology* 10 (3) : 1084–1094.
Cruz, A. and Beverley, S.M., "Gene replacement in parasitic potozoa", (Nov. 8, 1990), *Nature* 348 (6297) : 171–173.
Lebowitz, J.H. et al., "Development of a stable *Leishmania* expression vector and application to the study of parasite surface antigen genes", (Dec. 1990), *Proc. Natl. Acad. Sci. USA* 87:9736–9740.
te Riele, H. et al., "Consecutive inactivation of both alleles of the pim–1 proto–oncogene by homologous recombination in embryonic stem cells", (Dec. 13,1990), *Nature* 348:649–651.
Coburnl C.M. et al., "Stable DNA transfection of a wide range trypanosomatids" (1991), *Molecular and Biochemical Parasitology* 46:169–180.

*Primary Examiner*—Nancy Degen
*Attorney, Agent, or Firm*—Testa Hurwitz & Thibeault, LLP

[57] ABSTRACT

Homozygous gene replacement can be created in unicellular diploid organisms by individually targeting each allele of a gene with genetic constructs containing two different and independent selectable markers. Selection for both markers indicates replacement of both alleles of the gene, or portion thereof. The method can be used to study gene function in these organisms and to create mutant organisms such as attenuated strains of parasitic protozoans for use in live vaccines.

15 Claims, 6 Drawing Sheets

SEQUENCE LISTING (1) GENERAL INFORMATION:

(iii) NUMBER OF SEQUENCES: 1

(2) INFORMATION FOR SEQ ID NO:1:

(i) SEQUENCE CHARACTERISTICS:
      (A) LENGTH: 30 base pairs
      (B) TYPE: nucleic acid
      (C) STRANDEDNESS: single
      (D) TOPOLOGY: linear    (ii) MOLECULE TYPE: cDNA       (xi) SEQUENCE DESCRIPTION: SEQ ID NO:1:

CGGGATCCAC     TAGTGATGAA     AAAGCCTGAA     30

DOUBLE TARGETED GENE REPLACEMENT IN UNICELLULAR DIPLOID ORGANISMS

RELATED APPLICATIONS

This is a continuation of application Ser. No. 08/489,701 filed on Jun. 13, 1995, now abandoned, which is a continuation of application Ser. No. 08/066,718 filed on May 24, 1993, now abandoned, which is a continuation-in-part of application Ser. No. 07/744,313 filed on Aug. 13, 1991, now abandoned.

BACKGROUND OF THE INVENTION

Homologous gene replacement offers a powerful method for altering and testing gene function (Capecchi, M. (1989) Science 244:1288–1292). In diploid organisms with a sexual cycle, a single heterozygous replacement is first obtained which is then rendered homozygous by sexual crossing. Although Leishmania are diploid at most loci, they appear to be predominantly or exclusively asexual in nature and in the laboratory (Tait, A. (1983) Parasitology 86:29–57; Tibayrenc, M. et al. (1990) Proc. Natl. Acad. Sci. USA 87:2414–2418; Panton, L. J. et al. (1991) J Protozoology 38:224–228). This situation is not unusual, as many diploid unicellular organisms lack a sexual cycle (Whelan, W. L. (1987) CRC Critical Reviews 14:99–170) or possess one that is not readily manipulable.

Methods have been developed that can be utilized to obtain homozygous mutant lines from a heterozygous parent, in the absence of a manipulable sexual cycle. Parasexual crossing has been utilized in some organisms; however, parasex has not been demonstrated in organisms such as Leishmania. Another approach is the use of UV radiation or other agents to induce mitotic recombination following transformation, as shown in Candida albicans (Kelley, S. L. et al. (1988) Science 241:1813–1815). The disadvantage is that mutagenic agents may create secondary mutations that cannot be removed by back-crossing.

Improved methods of homozygous gene replacement in diploid organisms which lack a sexual cycle are needed.

SUMMARY OF THE INVENTION

This invention pertains to methods of creating homozygous gene replacements resulting in complete loss of targeted gene function in asexual diploid organisms and to the mutant asexual diploid organisms carrying the homozygous gene replacements.

The method comprises targeting both alleles of the gene to be replaced with constructs employing two different, independent selectable markers. The first construct comprises DNA encoding a first selectable marker flanked by DNA complementary to flanking regions of one allele of the gene, or portion thereof, to be replaced and the second construct comprises DNA encoding the different selectable marker flanked by DNA complementary to flanking regions of the other allele of the gene, or portion thereof. The organism is transfected with the constructs which recombine and replace the targeted gene at each allele and transfected organisms are selected for expression of both selectable markers as indicative of homozygous replacement of the gene.

The method of this invention can be used in protozoans and in asexual, diploid yeast to enable functional genetic testing in these organisms. In addition, the method can be used to generate attenuated forms of parasitic organisms for use in live parasite vaccines or vaccine vehicles.

DETAILED DESCRIPTION OF THE INVENTION

Homozygous gene replacements can be created by targeting individually each allele of the gene to be replaced with DNA constructs containing different, independent selectable markers. According to the method of this invention, the organism is transfected with two DNA constructs. The first construct comprises DNA encoding a first selectable marker flanked by DNA complementary to 5' and 3' flanking regions of one allele of the gene, or portion thereof, to be replaced. The second construct comprises DNA encoding the different selectable marker flanked by DNA complementary to flanking regions of the other allele of the gene. The organism is transfected with the constructs of the gene. The organism is transfected with the constructs resulting in the integration of the constructs into each allele in place of the targeted gene. The transfected organisms are selected for expression of both selectable markers as indicative of homozygous replacement of the gene. This yields diploid unicellular organisms having an endogenous chromosomal gene, or portion thereof, replaced at both alleles with two different and independent selectable markers.

The method of this invention can be used to generate double gene replacements in any unicellular diploid organism which exhibits a frequency of homologous gene replacement sufficient to permit two successive rounds of gene targeting. The method is especially useful for creating double gene replacements in organisms which lack a sexual cycle or possess one that is experimentally difficult to use. Examples of such organisms include Trypanosomatid protozoans such as trypanosomes and Leishmania and yeast such as Saccharomyces cerevisiae and Candida albicans. Leishmania embraces all species classified within the genus Leishmania including L. major, L. tropica, L. aethiopica, L. donovani, L. infantum, L. chagasi, L. braziliensis, L. panamaensis, L. guyanaensis, L. amazonesis, L. mexicana and L. venezuelaensis.

The DNA constructs for targeted replacement are constructed by standard techniques of gene targeting methodology. Typically, constructs are linear DNA fragments. The fragments can be assembled in a DNA vector, such as a plasmid, which permits production and isolation of sufficient quantities of DNA fragment for recombination with complementary chromosomal DNA of the organism.

The method can be used to replace a complete gene, a portion of a gene or several contiguous genes (e.g., contiguous multiple copies of a gene). DNA complementary to flanking regions of the DNA targeted for replacement can be obtained by isolation or by synthesis from known or determined genomic sequences. To replace the complete coding region of a gene, DNA complementary to the sequences flanking the 5' and 3' ends of the gene are used to flank the selectable marker. To replace a portion of the gene, gene sequences flanking the targeted portion of the gene are used. Flanking sequences can vary in length. In general, increased targeting frequencies are obtained with constructs having longer complementary flanking sequences (for example, 5 kb compared with 1.4 kb).

The selectable markers used in the method are typically markers which confer drug resistance. The markers should be suitable for stable integrative transfection into chromosomes of the unicellular organism. The markers should be independent so as to allow for simultaneous maintenance and selection of both markers in transfected organisms. Preferred selectable markers are the gene encoding neomycin transferase, which confers resistance to aminoglycosides such as G418, and the gene encoding hygromycin phosphotransferase, which confers resistance to hygromycin B. The genes can be obtained from available sources or synthesized.

The cells are preferably transfected by electroporation. In preferred embodiments, the organism is transfected sequentially with the constructs. The cells are transfected with the first construct and then cells selected for acquisition of the marker carried by the first construct are transfected with the second construct and selected for homozygous gene replacement. In some organisms, simultaneous transfection may be possible.

The amount of construct used to transfect cells is designed to maximize homologous recombination. In Leishmania, for example, simple replacement events are favored by relatively low DNA amounts (for example, <5 $\mu$g per $4 \times 10^7$ cells and 0.4 ml of electroporation medium).

Transfected cells can be selected for homozygous gene replacement by standard techniques. For example, if the selectable markers confer drug resistance, the organisms can be selected for resistance by culture in a culture medium containing the drugs and any other nutritional supplement that might be necessary to grow the mutant organism (for example, the nutrient required by an auxotrophic mutant). Disruption of the targeted gene can be confirmed by molecular analysis, e.g., Southern blot analysis, DNA sequencing and molecular karyotyping. In addition, selected cells can be examined for disruption of function of the replaced gene.

The method of this invention can be used to create strains of parasitic protozoans or yeasts of attenuated virulence for use in live vaccines. For this purpose, single-copy genes which are essential for growth of the organism in its host in vivo but not for growth in vitro are targeted for replacement. Examples of important metabolic enzymes encoded by single-copy genes in Trypanosomatid protozoans, for example, are DHFR-TS (Cruz, A. and Beverley, S. M. (1990) *Nature* 348:171–174) and trypanothione reductase (Kelley, S. L. et al. (1988) *Science* 241:1813–1815). These genes can be replaced in infective strains of Leishmania or trypanosomes to produce infective strains of attenuated virulence for vaccinations of humans.

Attenuated strains of infective unicellular organisms produced by the method of this invention can also be used as vehicles for delivery of immunogens of another organism for vaccination. The attenuated organism can be transfected either chromosomally or extrachromosomally with a gene encoding a protective immunogen of a pathogen. If desired, the organism can be designed to overproduce the immunogen by recombinant DNA methodologies.

The attenuated strains can be administered for vaccination according to standard protocols.

The invention is illustrated further by the following exemplification of the homozygous replacement of the dhfr-ts gene in Leishmania.

EXAMPLES

Example I

Materials and Methods
Construction of pX63-HYG

The HYG resistance gene within pUC-HYGR (Egelhoff, T. T. et al. (1989) *Mol. Cell. Biol.* 9:1965–1968) was used as a template for PCR amplification, using the 5' oligonucleotide primer CGGGATCCACTAGTG/ATGAAAAAGCCTGAA (SEQ ID NO:1) (which contains synthetic BamHI and SpeI sites joined to the first 15 bp of the hph coding region (Gritz, L. and Davies, J. (1983) *Gene* 25:179–188) and the M13 reverse sequencing primer (New England Biolabs). The predicted 1.05 kb product was obtained, digested with SpeI (5' site) and XbaI (3' site, arising from the polylinker in pUC-HYGR), and isolated after agarose gel electrophoresis. It was then inserted into pX63-NEO, a modified version of the expression vector pX differing only in the bacterial vector portion (LeBowitz, J. H. et al (1990) *Proc. Natl. Acad. Sci. USA* 87:9736–9740; LeBowitz, J. H. et al. (1991) *Gene* 103:119–123). The 0.9 kb SpeI NEO fragment of pX63-NEO was removed by SpeI digestion and replaced with the HYG cassette, yielding pX63-HYG.

Figure 1A:
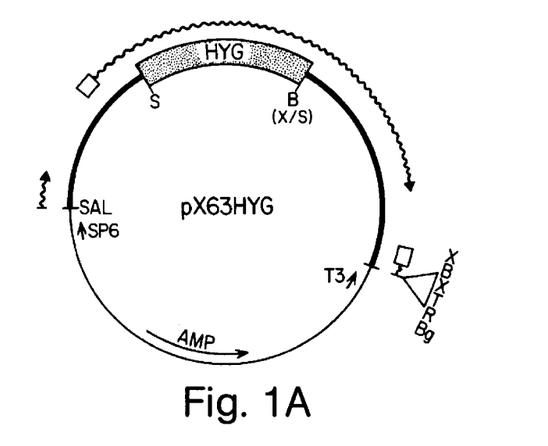
FIGS. 1A–1C show A) a map of the plasmid pX63-HYG which carries the gene encoding hygromycin phosphotransferase flanked by DNA complementary to flanking regions of the dhfr-ts locus of Leishmania major, B) the structure of the dhfr-ts locus in Leishmania major and the planned NEO and HYG replacements in each chromosome and C) the predicted restriction fragments obtained in Southern analysis for the chromosomes.

A map of pX63-HYG is shown in FIG. 1. The light line represents the bacterial vector sequences (pSP6/T3); the orientation of the SP6 and T3 phage promoters are shown by small arrows. Leishmania derived sequences are marked by heavy lines; these sequences are the same ones present in pX (Mansour, S. L. et al (1988) *Nature* 336:348–352). The hph gene cassette is indicated by the stippled box (HYG). The small open boxes and the arrowheads attached to wavy lines represent the sites of miniexon addition and polyadenylation present in normal Leishmania DNA, sequences which are functional in the pX vector (Mansour, S. L. et al. (1988) *Nature* 336:348–352); the wavy line represents the expected chimeric RNA. Relevant restriction sites are S, SpeI I; B, Bam HI, Bg, BgI II, X, Xma(Sma) I; T, Sst I, R, EcoRI; SAL, Sal I.

Constructs in which the HYG cassette was inserted in the opposite orientation to normal Leishmania transcription were also obtained (pX63-GYH; not shown).

Cells, Culture, Transfection

All lines were derived from the *Leishmania major* LT252 line. CC-1 is a diploid wild-type clonal line (designated +/+; Kapler, G. M. et al. (1990) *Mol. Cell. Biol.* 10:1084–1094), and E-27'C3 is a heterozygous line formed by replacement of one dhfr-ts allele with NEO (designated +/neo; Cruz, A. and Beverley, S. M. (1990) *Nature* 348:171–174). Cells were cultured in M199 medium and transfected by electroporation as described (500 $\mu$F, 2.25 kV/cm; Kapler, G. M. et al. (1990) *Mol. Cell. Biol.* 10:1084–1094). G418 (Geneticin; BRL) was utilized at 16 $\mu$g/ml in plates and 6 $\mu$g/ml in liquid culture; corresponding concentrations of hygromycin B (Sigma) were 32 and 16 $\mu$g/ml. KS supplements (10 $\mu$g ml$^{-1}$ thymidine, 25 $\mu$g ml$^{-1}$ glycine, 0.6 $\mu$g ml$^{-1}$ biopterin, 4 μg ml$^{-1}$ folate, 50 μM putrescine) were added to media in transfections expected to yield dhfr-ts null mutants (Cruz, A. and Beverley, S. M. (1990) *Nature* 348:171–174). For nutritional tests, cells were cultivated in DMENF medium which is FD+B medium (Petrillo-Peixoto, M. P and Beverley, S. M. (1987) *Antimicrob. Agents Chemotherapy* 31:1575–1578) in which serum albumin is replaced by 10% heat-inactivated fetal bovine serum. This semi-defined medium contains biopterin and lacks exogenous folate and thymidine, and can support parasite growth indefinitely.

Karyotype and Southern analysis

The following methods were performed as described: preparation of Leishmania chromosomes (Beverley, S. M. (1988) *Nucleic Acids Res.* 16:925–938); separation of chromosomes by pulsed field electrophoresis with a contour-clamped homogeneous electric field (CHEF) apparatus (Chu, G. et al. (1986) *Science* 234:1582–1585); digestion of chromosomes (Coburn, C. M. et al. (1991) *Mol. Bioch. Parasit.* 46:169–180); Southern blot hybridization using Gene Screen Plus membranes (DuPont-NEN; Ellenberger, T. E. and Beverley, S. M. (1989) *J. Biol. Chem.* 264:15094–15103); radiolabelling of probes by random priming (Feinberg, A. P. and Vogelstein, B. (1983) *Anal. Biochem.* 132:6–13); and γ-irradiation to linearize circular DNAs (Beverley, S. M. (1989) *Anal. Biochem.* 177:110–114).

Results

Hygromycin resistance as a selectable marker in Leishmania

Although a number of hygromycin resistance cassettes are available, most retain one or more out-of-frame ATG codons immediately upstream of the presumptive initiation codon of the *E. coli* hph gene (Gritz, L. and Davies, J. (1983) *Gene* 25:179–188). Since their potential effect on HYG expression in Leishmania was unknown, we utilized PCR amplification to remove these upstream ATGs. This HYG coding region cassette was then substituted for the NEO cassette in the vector pX63-NEO (LeBowitz, J. H. et al. (1990) *Proc. Natl. Acad. Sci USA* 87:9736–9740) to yield the vector pX63-HYG (FIG. 1A).

We determined the concentration of hygromycin B which inhibited the rate of Leishmania growth by 50% (EC$_{50}$) to be 10 μg/ml in liquid culture. Since previous studies showed that the G418 concentration required in plating studies was about 2.4 times the EC$_{50}$ (Kapler, G. M. et al. (1990) *Mol. Cell Biol.* 10:1084–1094; Coburn, C. M. et al. (1991) *Mol. Bioch. Parasit.* 46:169–180), pX63-HYG transfected-*L. major* were plated on semi-solid medium containing 32 μg hygromycin B/ml. Within two weeks after transfection 345 colonies/10 μg pX63-HYG were obtained, comparable to the results obtained with G418 selection and the plasmids pR-NEO and pX (15– 60 colonies/μg DNA; Kapler, G. M. et al. (1990) *Mol. Cell Biol.* 10:1084–1094; LeBowitz, J. H. et al. (1990) *Proc. Natl. Acad. Sci. USA* 87:9736–9740), pX63-GYH, which contains the HYG cassette in the antisense orientation, did not yield any colonies on hygromycin B-containing plates.

The molecular karyotypes of several clonal pX63-HYG transfectants that had been maintained in hygromycin selective media for more than 100 cell doublings were identical to that of the parental CC-1 line (FIG. 2A). Chromosomes from the indicated lines were separated by pulsed field electrophoresis (55 sec pulse, 48 hr). The ethidium bromide-stained gel is shown. Lane 1, line E26-pX63HYG-clone A; lane 2, line E26-pX63HYG-clone B; lane 3, wild-type (+) *L. major*. Molecular weight markers consisted of lambda-concatemers.

Figure 2:
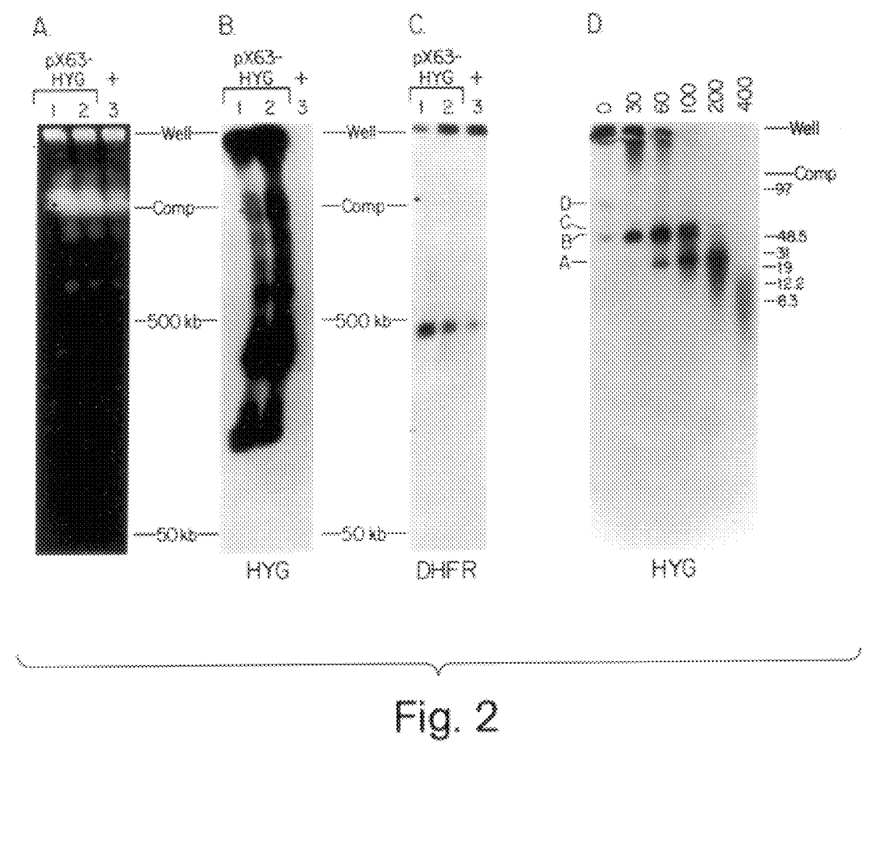
FIGS. 2A–2D show gel electrophoretic analyses of pX63-HYG transfectants.

The gel shown in panel A of FIG. 2 was subjected to Southern blot hybridization successively with coding region probes for HYG (FIG. 2, panel B; 1.05 kb PCR product) or DHFR (FIG. 2, panel C; 1.2 kb PstI-EcoRV fragment of the *L. major* DHFR-TS gene (Marsh, J. L. et al. (1984) *Gene* 32:481–485), isolated after first cloning this fragment into PstI+ EcoRV digested plC19H (Marsh, J. L. et al. (1984) *Gene* 32:481–485). Hybridization to a HYG probe was observed in the transfectant lines but not in the CC-1 line (FIG. 2B, lanes 1 and 2 vs. 3). The predominant hybridizing DNAs had apparent sizes of 280 and 400 kb, and some hybridization was also observed to the sample well. These DNAs exhibited pulse time dependent relative mobility, a hallmark of circular DNAs (compare FIG. 2B, lanes 1 and 2 with FIG. 2D, lane 0).

γ-irradiation analysis was used to introduce a limited number of double stranded breaks, as circular but not chromosomal DNAs yield new discrete linear fragments after this treatment (Beverley, S. M. (1989) *Anal. Biochem.* 177:110–114). Chromosome samples from line E26-pX63HYG-clone B were washed in 10 mM Tris, 1 mM EDTA, pH 7.4 and subjected to γ-irradiation as described (Beverley, S. M. (1989) *Anal. Biochem.* 177:110–114). The DNAs were separated by pulsed field electrophoresis (4 sec pulse, 18 hr), and analyzed by Southern blot hybridization with the HYG probe described in panel B. The dosage of γ-irradiation (in kRads) used for each sample is indicated above the autoradiogram shown in panel D. Molecular weight markers were lambda oligomers and the BRL high molecular weight marker.

As expected, γ-irradiation of DNA from line E26-pX63HYG-clone B yielded two new linear DNA fragments, labeled A and C in FIG. 2B. We estimated the sizes of these new fragments at the lowest dose of γ-irradiation, where the effect of comigrating broken chromosomal DNAs was minimal (lane 60 in FIG. 2D). Fragments A and C were estimated to be 28 and 52 kb, respectively, suggesting that this transfectant contains tetrameric and octameric extrachromosomal circular forms of the 6.2 kb pX63HYG plasmid. Hybridization with a DHFR-TS probe revealed only the wild-type DHFR-TS chromosome in all three lines (FIG. 2C), suggesting that integration of pX63-HYG DNA had not occurred. These data established that the HYG resistance cassette functioned extrachromosomally as expected in Leishmania.

Independence of HYG and NEO resistance markers

Preliminary tests showed that in liquid culture, Leishmania transfected with pX63-HYG remained sensitive to G418 while those bearing pX (carrying NEO) remained sensitive to hygromycin B. In plating tests of line E26-pX63HYG-clone 1, 121 ±15 colonies (average±standard deviation) were obtained on plates containing 32 μg/ml hygromycin B while none were obtained on those containing 16 μg/ml G418. Correspondingly, plating of line E15-pX-clone A1 yielded 162±52 colonies on G418 plates while none were obtained on hygromycin B plates.

One experiment was performed to test whether both HYG and NEO vectors could be introduced simultaneously. Five μg DNA of both pX63-HYG and pBg94NEOA (Cruz, A. and Beverley, S. M. (1990) *Nature* 348:171–174) were mixed, transfected into Leishmania, and the cells divided and plated on media containing G418, hygromycin B, or both drugs. On single drug plates 87 colonies were obtained, while on double drug plates 15 colonies were obtained (17%). This shows that transfected Leishmania frequently take up more than one DNA molecule. In subsequent studies we have shown that clonal lines previously transfected with extrachromosomal NEO constructs can be subsequently transfected with pX63-HYG derivatives by plating on media containing both drugs, with no change in plating efficiency (data not shown).

HYG as a selectable marker for gene replacement

Figure 1B:
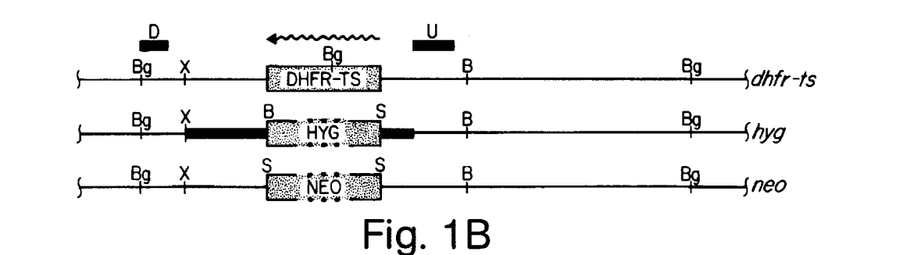
Figure 4:
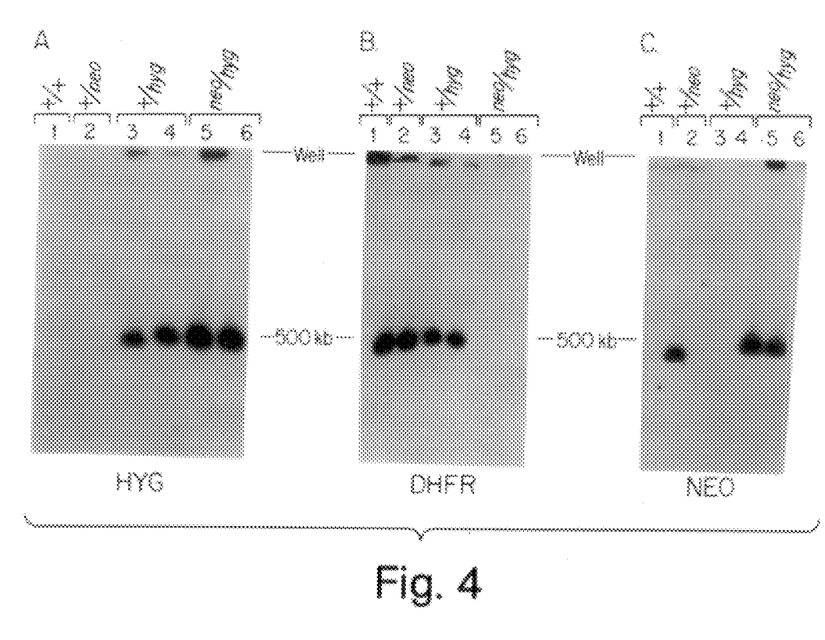
FIGS. 4A–4C show Southern blot analyses of targeted gene replacements.

The structure of the dhfr-ts locus and planned NEO and HYG replacements are shown in FIG. 1B. The top line (dhfr-ts) depicts the wild-type chromosome; the location of the DHFR-TS coding region is shown by the open box. The second line (hyg) depicts the planned HYG replacement chromosome, and the third line (neo) depicts the planned NEO replacement chromosome. The HYG and NEO coding regions are shown by boxes with dashed lines, as these coding regions are about 1 kb smaller than DHFR-TS. The 3.3 kb HYG targeting fragment is shown by heavier lines on the hyg map. The hybridization probes U and D utilized in FIG. 4 are shown above the dhfr-ts map. The wavy line represents the direction of transcription.

To test whether HYG was suitable as a marker for gene replacement, we transfected the 3.3 kb SalI-SmaI fragment of pX63-HYG (FIGS. 1A, 1B). This fragment contains only 0.9 and 1.4 kb of 5' and 3' DNA which normally flanks the L. major dhfr-ts coding region, whereas a previously utilized targeting fragment contained 5 and 2 kb respectively of dhfr-ts flanking DNA (Cruz, A. and Beverley, S. M. (1990) Nature 348: 171–174). We utilized less than 5 µg of the targeting DNA fragment, since simple replacement events in Leishmania are favored by relatively low DNA amounts (Cruz, A. and Beverley, S. M. (1990) Nature 348:171–174). 2–4 colonies/µg targeting fragment were obtained, 5–10% of the yield obtained with circular pX63-HYG. A similar result was obtained with the analogous 3.3 kb fragment from pX (containing the NEO marker) after plating on G418-containing media. In contrast, the larger NEO targeting fragment yielded colonies at 20–100% the efficiency of the circular controls (Cruz, A. and Beverley, S. M. (1990) Nature 348:171–174), consistent with studies in other species showing increased targeting frequencies with fragments bearing longer homologous sequences (Shulman, M. J. et al. (1990) Mol. Cell. Biol. 10:4466–4472.; Thomas, K. R. and Capecchi, M. R. (1987) Cell 51:503–512).

Figure 3:
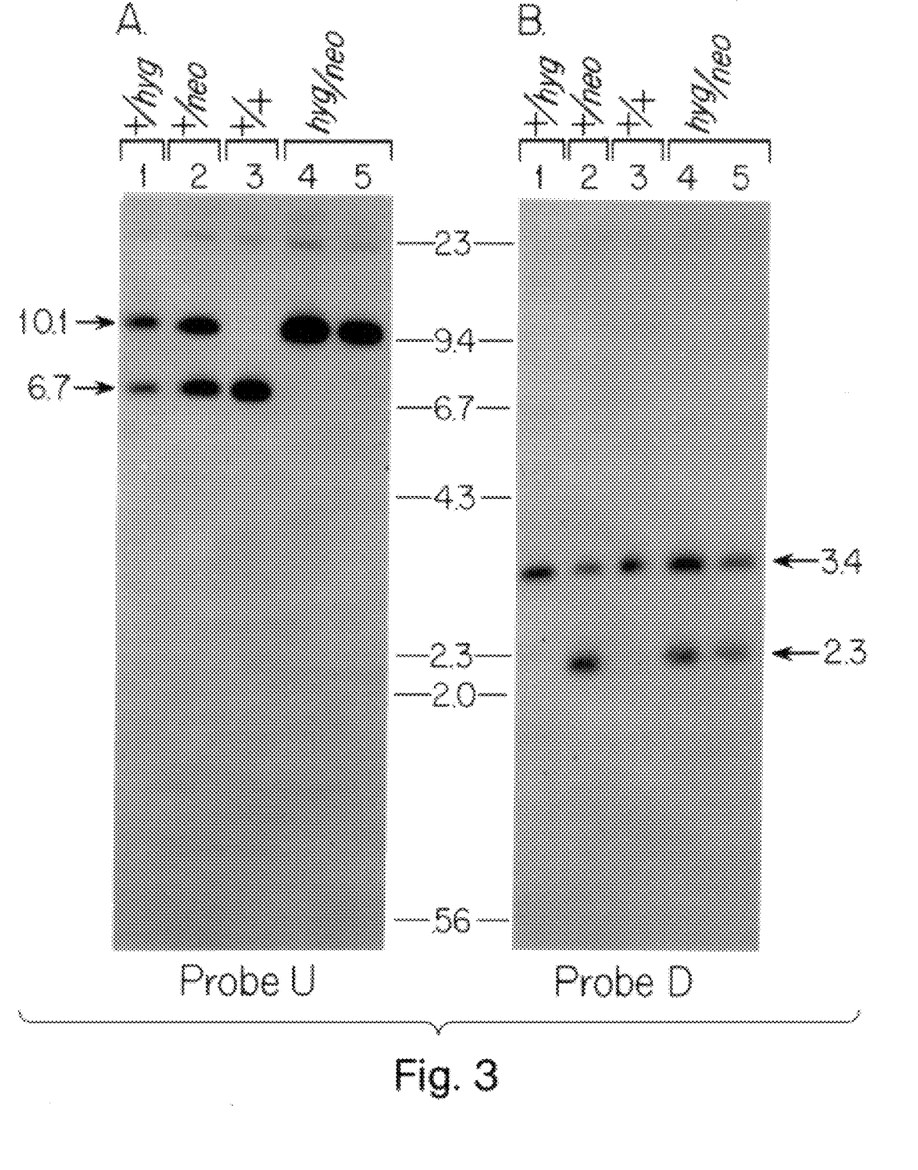
FIGS. 3A–3B show molecular karyotype analyses of targeted gene replacements.

Molecular karyotype analysis of nine clonal derivatives arising from these experiments suggested that all possessed the planned targeted gene replacement (data for two clones are shown in FIG. 3). Chromosomes from the indicated clonal lines were separated and analyzed by Southern blot hybridization as described in the legend to FIG. 2. Hybridization probes were the coding regions for HYG (panel A), DHFR (panel B), and NEO (panel C; 0.9 kb SpeI fragment from pSpeNEOA (Kapler, G. M. et al. (1990) Mol. Cell. Biol. 10:1084–1094). Different blots were used for each probe. The genotype inferred is indicated; lane 1, wild-type L. major; lane 2 E2–7D2 (transfected with NEO targeting fragment only; 4); lanes 3 and 4, lines E8-5C5 and E8-5'Al (transfected with HYG targeting fragment only); lanes 5 and 6, E10-5B5 and E10-5A3, which are line E2-7'C3 (neo/+) transfected with the HYG targeting fragment).

Hybridization with an HYG probe revealed a single linear chromosome of about 500 kb, as did hybridization with a DHFR-TS probe (FIGS. 3A, 3B, lanes 3 and 4). This suggested that these lines now contained one wild-type and one HYG-replacement chromosome (+/hyg), which was tested by Southern blot analysis using appropriate probes and digests (FIG. 4). With hybridization probe U and BglII digests (FIGS. 1B, 1C), a 6.7 kb fragment arises from the wild-type dhfr-ts locus while a 10.1 kb fragment is predicted from the planned replacement. Accordingly, wild-type (+/+) Leishmania showed only the 6.7 kb fragment (FIG. 4A, lane 3), while the HYG transfectants contained both the 6.7 and 10.1 kb fragments (FIG. 4A, lane 1). Analogous results were obtained In BamHI+SpeI digests with probe D (not shown). This confirms that these lines contain the planned replacement and are now genetically +/hyg at the dhfr-ts locus.

Replacement of the second allele of the DHFR-TS gene

By gene targeting we previously created lines heterozygous at the dhfr-ts locus, containing one chromosome with NEO replacing dhfr-ts (neo/+; Cruz, A. and Beverley, S. M. (1990) Nature 348:171–174). To create lines completely lacking dhfr-ts, one of these lines was employed as a recipient for the 3.3 kb HYG targeting fragment. Following electroporation, cells were plated on medium containing both drugs, and nutritional supplements shown previously to support the growth of dhfr-ts cells (Cruz, A. and Beverley, S. M. (1990) Nature 348:171–174). 2–4 colonies per µg HYG targeting fragment were obtained, a frequency comparable to that obtained with the wild-type recipient. Five of six transfectants analyzed exhibited a karyotype consistent with the planned replacement (data for two lines are shown in FIG. 3). In these cells the HYG hybridization probe identified a single 500 kb chromosome (FIG. 3A, lanes 5, 6), as did the NEO hybridization probe (FIG. 3C, lanes 5, 6). In contrast, the DHFR-TS hybridization probe did not identify any chromosome in these lines (FIG. 3B, lanes 5, 6). These data showed that the dhfr-ts gene had been lost.

Figure 1C:
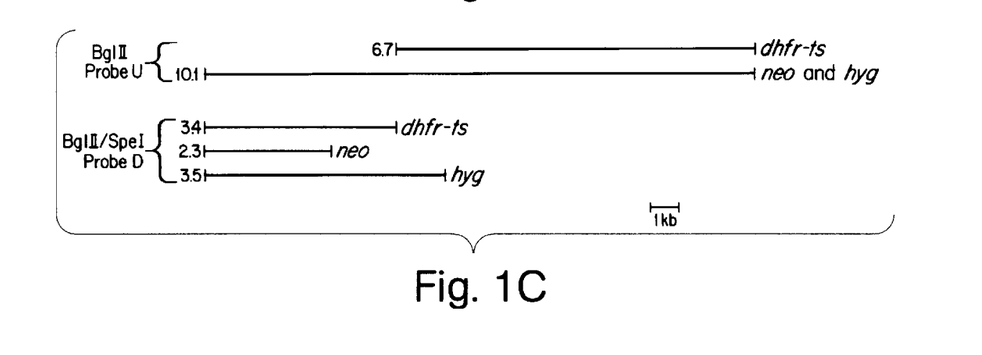

Southern blot analysis (FIG. 4) confirmed that these lines contained only the planned NEO and HYG replacements. DNAs from the indicated lines were digested with either BgI II (panel A) or BglII+Spe I (panel B), separated on 0.8% agarose gels, and subjected to Southern blot hybridization with hybridization probes U (panel A) or D (panel B) depicted in FIG. 1B. The predicted fragment sizes depicted in FIG. 1C are marked by arrows; the positions of molecular weight markers are shown between panels A and B.

With BgIII digests and probe U, only the 10.1 kb fragment expected for both the NEO and HYG replacements was observed (FIG. 4A, lanes 4, 5); in contrast, a +/neo line additionally exhibited the 6.7 kb wild-type fragment (FIG. 4A, lane 2). With BgIII+SpeI digests and probe D (FIGS. 1B, 1C), both the 2.3 NEO replacement fragment (FIG. 4B, lane 2) and the 3.5 kb HYG replacement fragment were observed (FIG. 4B, lanes 4, 5). Analogous data were obtained with probe U and BamHI+SpeI digests, which test the structure from the 5' side (not shown). These data indicated that the planned replacement had occurred, yielding transfectants that were now neo/hyg at the dhfr-ts locus.

Phenotype of dhfr-ts disruptants

Figure 5:
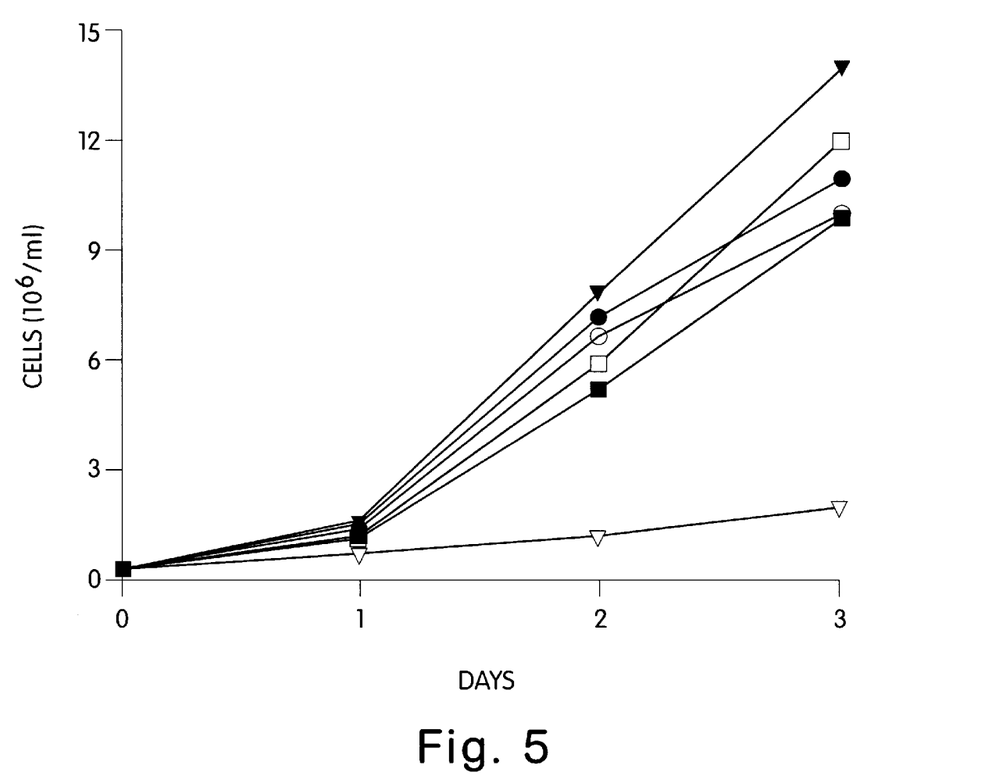
FIG. 5 shows the growth curves for +/+, +/hyg and neo/hyg Leishmania in the presence and absence of thymidine.

Leishmania were grown in DMENF medium, except that the media for the neo/hyg line additionally contained 10 µg/ml thymidine. The growth curves are shown in FIG. 5. Stationary phase cells were inoculated into fresh DMENF medium without (open symbols) or with 10 µg/ml thymidine (closed symbols), and cell density monitored with a Coulter counter. (□), +/+ L. major; (O), +/hyg line E8-5'Al: (V), neo/hyg line E10-5C5. The neo/hyg line did not exhibit additional growth at increased times or after resuspension into fresh medium (not shown).

The +/+ or hyg/+ lines grew at comparable rates in both media. In contrast, the neo/hyg line grew only in the presence of thymidine (FIG. 5). These data suggested that the sole essential role of DHFR-TS in the defined medium was in provision of thymidine.

We describe the development of the hygromycin B resistance gene (HYG) as a second selectable marker for stable DNA transfection of Leishmania. The properties of transfection vectors containing this marker are similar to those bearing the NEO marker previously utilized in Leishmania: the efficiency of DNA transfection is comparably high, previously developed extrachromosomal vectors now bearing the HYG marker remain extrachromosomal, and targeting fragments employing HYG can be utilized to conduct gene replacement at the dhfr-ts locus. As in other organisms (Blochlinger, K. and Diggelmann, H. (1984) *Mol. Cell Biol.* 4:2929–2931), the mechanisms of resistance mediated by the HYG and NEO genes are independent in Leishmania. This permits the simultaneous introduction and maintenance in Leishmania of constructs bearing both markers, in either extrachromosomal or chromosomal locations. The availability of a second, independent selectable marker will expand the kinds of tests of gene function that can be pursued in this organism.

Although the relative frequency of homologous gene replacement in Leishmania is high, the fact that Leishmania is a functionally asexual diploid requires that both alleles be modified prior to functional testing. The availability of a second selectable marker allowed us to overcome this problem. Null mutants at dhfr-ts were obtained by two rounds of gene targeting, first with NEO-containing and then with HYG-containing targeting vectors (the order is unimportant; unpublished data). The efficiency of each step was comparable. Although previous studies suggested that it should be possible to obtain simultaneous replacement of both dhfr-ts alleles (Cruz, A. and Beverley, S. M. (1990) *Nature* 348:171–174), we have not been able to accomplish this by transfection of the NEO and HYG targeting fragments simultaneously. We presume that this reflects the low cumulative frequency expected for simultaneous transfection and replacement. Improved procedures may remove this limitation at the dhfr-ts locus in the future, however for loci in which the viability of the null mutant is unknown the two step procedure may be preferable.

Example II

Laboratory mice were used as a test system as they constitute an excellent model for the pathology of human leishmaniasis. These experiments were performed in collaboration with the laboratory of Dr. Richard Titus of the Harvard School of Public Health.

Safety

To test the safety of the lines generated by double gene targeting of the dhfr-ts locus of Leishmania, these were injected at extremely high levels ($10^8$ parasites) into a very susceptible strain of mice (Balb/c). Controls included the parental line CC-1 (the parent of the double-targeting line) and an independent virulent line. After 1 month both of the control lines induced severe infections, while after more than 4 months no sign of a parasitic lesion in mice injected with the double-targeted lines was observed.

Efficacy in vaccination

The ability of the dhfr-ts double gene replacement line of Leishmania to induce a successful immunization was tested by intravenous injection of genetically susceptible mice, first with an immunizing dose of live parasites ($10^6$), followed 1 month later by cutaneous injection of a challenge dose of a highly virulent strain ($10^5$ parasites). Unimmunized mice developed characteristic lesions in less than 1 month, while immunized mice did not develop a lesion for more than 3 months. Eventually these lines, however, did develop leishmaniasis. The efficacy of the line can be improved by exploring variables such as immunizing dose. However, even at this stage these results are superior to many previous vaccine attempts published in the literature for leishmaniasis.

Example III

Figure 6:
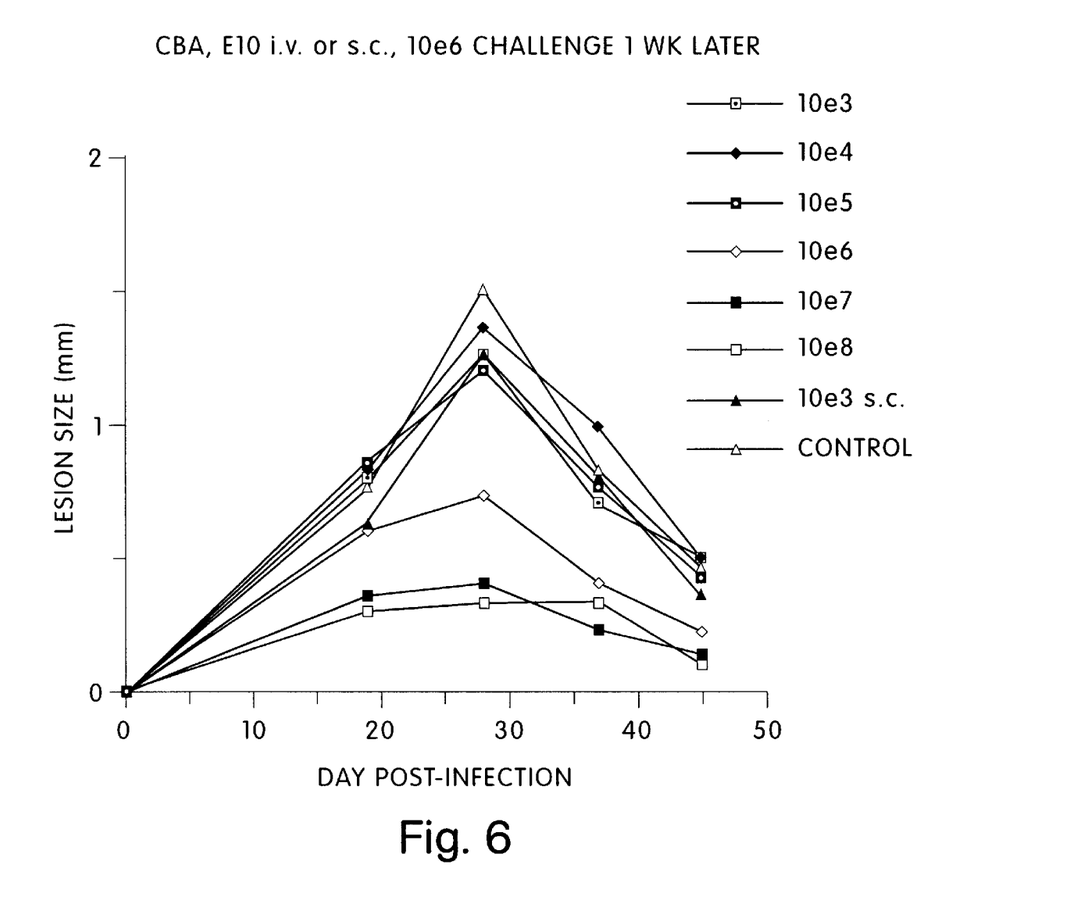
FIG. 6 shows the effect of the number of immunizing parasites injected intravenously in CBA mice on the ability of the mice to withstand challenge with a highly virulent strain of Leishmania major.

Experiments were performed in the CBA strain of mice—the standard model for human leishmaniasis caused by *Leishmania major*. FIG. 6 documents the course of infection by a fully virulent strain of *Leishmania major* (LV39 clone 5), after inoculation into mice that had been vaccinated with the avirulent DHFR-TS⁻ strain obtained by gene targeting as described in this application. In these experiments mice (CBA strain) are first injected with varying doses of the vaccination strain and one week later challenged with the virulent strain to assess the degree of protection conferred. In all cases, $10^6$ cells of the virulent strain were inoculated subcutaneously. The site of injection of the vaccination strain was either intravenous (iv) or subcutaneous (sc). The data show that upon intravenous vaccination with $10^7$ or great or DHFR-TS⁻ parasites, considerable protection against subsequent challenge was obtained.

Equivalents

Those skilled in the art will recognize, or be able to ascertain using no more than routine experimentation, numerous equivalents to the specific procedures described herein. Such equivalents are considered to be within the scope of this invention and are covered by the following claims.

We claim:

1. In a method of producing a genetic mutant by homologous recombination, wherein an organism is transfected with two different DNA sequences, the improvement comprising:
   a) transfecting a unicellular diploid organism with first and second nucleic acid constructs, said first construct comprising a first selectable marker flanked by nucleotide sequences complementary to 5' and 3' flanking regions of a first allele of a genetic locus to be replaced, and said second construct comprising a second selectable marker flanked by nucleotide sequences complementary to 5' and 3' flanking regions of a second allele of the genetic locus to be replaced under conditions to promote deletion and replacement of said genetic locus by said DNA sequences;
   b) selecting for replacement and loss of said genetic locus from the genome of said unicellular diploid organism by detecting expression of both said different marker genes; and
   c) isolating a genetic mutant of said unicellular diploid organism that expresses both said selectable marker genes, said mutant having lost both said alleles of said genetic locus via replacement with both said selectable markers.

2. The method of claim 1 wherein said unicellular diploid organism is transfected simultaneously with said two different DNA sequences.

3. The method of claim 1 wherein said genetic locus comprises a first and a second allele.

4. The method of claim 1 wherein said genetic locus comprises a gene.

5. The method of claim 1 wherein loss of said genetic locus provides for conditional auxotrophy.

6. The method of claim 1 wherein said genetic locus modulates persistence of said unicellular diploid organism in a host in vivo and is not required for growth of said organism in vitro.

7. The method of claim 1 wherein said unicellular diploid organism is a protozoa.

8. The method of claim 1 wherein said protozoa is a parasitic protozoa.

9. The method of claim 8 wherein said parasitic protozoa is a member of the genus Leishmania.

10. A genetic mutant of a unicellular diploid organism produced according to the method of claim 1.

11. A unicellular diploid organism, the genome of which is devoid of a naturally-occurring genetic locus that modulates virulence of said organism in a host, said genetic locus having been deleted and replaced by at least two different selectable marker genes.

12. The organism of claim 11 wherein said genetic locus modulates persistence of said organism in said host in vivo and is not required for growth of said organism in vitro.

13. The organism of claim 11 wherein said unicellular diploid organism is a protozoa.

14. The organism of claim 11 wherein said protozoa is a parasitic protozoa.

15. The organism of claim 14 wherein said parasitic protozoa is a member of the genus Leishmania.

* * * * *

UNITED STATES PATENT AND TRADEMARK OFFICE
CERTIFICATE OF CORRECTION

PATENT NO.    : 5,955,333
DATED         : September 21, 1999
INVENTOR(S)   : Stephen M. Beverley et al.

It is certified that error appears in the above-identified patent and that said Letters Patent is hereby corrected as shown below:

Column 1 line 3 immediately following the title insert --Government Funding:
This invention was supported by NIH grant numbers AI-21903 and AI-29646 and the government has certain rights to the invention.--

Signed and Sealed this

Thirteenth Day of June, 2000

*Attest:*

Q. TODD DICKINSON

*Attesting Officer*    *Director of Patents and Trademarks*